United States Patent [19]

Jayaraman

[11] Patent Number: 5,755,781
[45] Date of Patent: May 26, 1998

[54] EMBODIMENTS OF MULTIPLE INTERCONNECTED STENTS

[75] Inventor: Swaminathan Jayaraman, Bangalore, India

[73] Assignee: Iowa-India Investments Company Limited, Virgin Islands (Br.)

[21] Appl. No.: 799,449

[22] Filed: Feb. 13, 1997

Related U.S. Application Data

[63] Continuation-in-part of Ser. No. 692,570, Aug. 6, 1996.

[51] Int. Cl.⁶ ............................................. A61F 2/06
[52] U.S. Cl. ........................................ 623/1; 623/12
[58] Field of Search ............................. 623/1, 11, 12; 606/194, 195, 198; 600/36

[56] References Cited

U.S. PATENT DOCUMENTS

| | | |
|---|---|---|
| 4,733,665 | 3/1988 | Palmaz . |
| 4,739,762 | 4/1988 | Palmaz . |
| 4,776,337 | 10/1988 | Palmaz . |
| 5,102,417 | 4/1992 | Palmaz . |
| 5,135,536 | 8/1992 | Hillstead .......................... 606/195 |
| 5,195,984 | 3/1993 | Schatz . |
| 5,383,892 | 1/1995 | Cardon et al. . |
| 5,421,955 | 6/1995 | Lau et al. . |
| 5,443,496 | 8/1995 | Schwartz et al. . |
| 5,443,498 | 8/1995 | Fontaine . |
| 5,449,373 | 9/1995 | Pinchasik et al. . |
| 5,545,210 | 8/1996 | Hess et al. ......................... 623/11 |

*Primary Examiner*—Debra S. Brittingham
*Attorney, Agent, or Firm*—James E. Larson; Larson & Larson, P.A.

[57] ABSTRACT

Embodiments of multiple interconnected stents each include a stent having a plurality of rows of slots with spaces between the slots being staggered in adjacent rows. In each embodiment, a plurality of stents are interconnected together with a connector. In one embodiment, the connector consists of a single flexible bar. In a second embodiment, the connector consists of a plurality of U-shaped members fused together. In a third embodiment, the connector consists of a plurality of slots orthogonal to the stent slots. In a fourth embodiment, a multiplicity of stents are interconnected together by flexible bars that are vertically staggered with respect to one another. In a fifth embodiment, adjacent stents are interconnected by flexible connectors resembling the letter "H". In a sixth embodiment, adjacent stents are interconnected by a plurality of vertically spaced horizontal bars. In a seventh, eighth and ninth embodiment, adjacent stents are interconnected by a plurality of flexible connectors resembling the letter "W", "V" and "U", respectively. The stents are prepared by coating a metal tube with a polymer, removing a predetermined portion of the polymer and removing the exposed metal by etching or electrolysis.

12 Claims, 9 Drawing Sheets

EMBODIMENTS OF MULTIPLE INTERCONNECTED STENTS

PRIOR APPLICATION

This application is a continuation-in-part from application Ser. No. 08/692,570 filed Aug. 6, 1996, now pending.

BACKGROUND OF THE INVENTION

The present invention relates to embodiments of multiple interconnected stents. In the prior art, stents are well known medical devices for use in opening and reinforcing the interior wall of a blood vessel. Sometimes, during transluminal imaging of the coronary or vascular system to repair a blood vessel in need of a stent, it is discovered that the length of the area of the repair is longer than that which could be repaired using a single stent of the usual length. Additionally, it is often the case that the area where repair and/or reinforcement is required extends around one or more curves in a tortuous path. Under such circumstances, a single segment stent will not adequately perform the job of strengthening and reinforcing the blood vessel. Since the individual stent must be made of a rigid construction to perform its reinforcing task, where a tortuous path of a blood vessel must be opened and/or reinforced, a plurality of stents must be interconnected together to cover the entire length of the area where reinforcement is necessary.

The following prior art is known to Applicant:

U.S. Pat. No. 4,733,665 to Palmaz

U.S. Pat. No. 4,739,762 to Palmaz

U.S. Pat. No. 4,776,337 to Palmaz

U.S. Pat. No. 5,102,417 to Palmaz

U.S. Pat. No. 5,195,984 to Schatz

U.S. Pat. No. 5,383,892 to Cordon et al.

U.S. Pat. No. 5,421,955 to Lau et al.

U.S. Pat. No. 5,443,496 to Schwartz et al.

U.S. Pat. No. 5,443,498 to Fontaine

U.S. Pat. No. 5,449,373 to Pinchasik et al.

Of the above-listed references, U.S. Pat. No. 5,102,417 to Palmaz, and the patents to Schatz, Cordon et al., Lau et al., Schwartz et al. and Pinchasik et al. are most noteworthy as teaching interconnection of a plurality of stents together. However, none of these references teaches the combination of a stent formed from a single fabrication method having the configuration disclosed herein along with the flexible articulation of interconnection with three or more stents disclosed herein.

SUMMARY OF THE INVENTION

The present invention relates to embodiments of multiple interconnected stents. The present invention includes the following interrelated objects, aspects and features:

(1) In a first aspect, in each of the embodiments of the present invention, a plurality or multiplicity of stents are interconnected together by interconnection means to form an elongated multiple stent configuration. In each embodiment, each stent is made from a rectangular piece of material formed in a roll with the facing edges fused together by means such as plasma energy fusing, LASER, ultrasound, or any other suitable means. Each stent so formed includes a configuration consisting of multiple rows of slots spaced by spaces with each space being staggered with respect to spaces of adjacent rows.

(2) Each separate embodiment of the present invention includes a plurality or multiplicity of stents such as described above. Each separate embodiment differs from the other embodiments as providing its own means of interconnection of adjacent stents. Thus, in a first embodiment, adjacent stents are interconnected by a single flexible resilient bar. In a second embodiment, adjacent stents are interconnected by means of U-shaped members fused together. In a third embodiment, adjacent stents are interconnected by an integral piece of material having slots extending orthogonal to the slots in the adjacent stents.

(3) In a fourth embodiment, similar to the first-mentioned embodiment, adjacent stents are interconnected by means of flexible resilient bars. However, different pairs of interconnected stents have bars vertically staggered with respect to other pairs of interconnected stents. In a fifth embodiment, adjacent stents are interconnected by virtue of a plurality of vertically spaced connectors resembling the letter "H".

(4) In a sixth embodiment, adjacent stents are interconnected by a multiplicity of vertically spaced elongated flexible resilient bars. In a seventh embodiment, adjacent stents are interconnected by virtue of a multiplicity of flexible resilient members resembling the letter "W".

(5) In an eighth embodiment adjacent stents are interconnected by a multiplicity of flexible resilient members resembling the letter "V" and in a ninth embodiment the flexible resilient members resemble the letter "U".

(6) In all of the embodiments of the present invention, the stents as interconnected together may be expanded within a blood vessel through the use of means such as, for example, an elastic or non-elastic balloon catheter or a mechanical spreader.

As such, it is a first object of the present invention to provide embodiments of multiple interconnected stents.

It is a further object of the present invention to provide such an invention wherein a plurality of stents are interconnected together employing various embodiments of interconnection means.

It is a still further object of the present invention to provide such an invention wherein each stent is formed by a rectangular piece of material formed into a roll with the facing edges fused together.

It is a still further object of the present invention to provide such a device wherein each stent is formed with a multiplicity of rows of slots having spaces therebetween with the spaces being staggered with respect to spaces in adjacent rows.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

Figure 1:
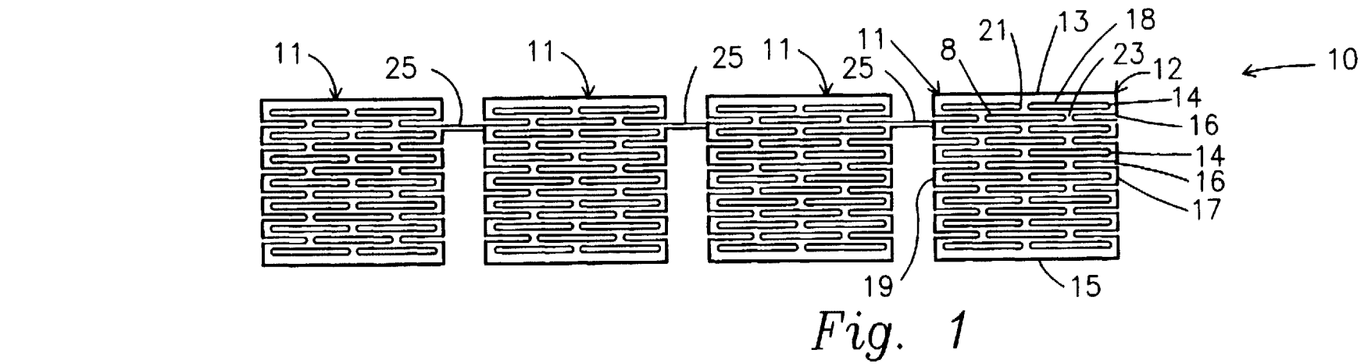
FIG. 1 shows a top view of a first embodiment of the present invention before the rectangular pieces are rolled and fused to form the multiple stents.
Figure 2:
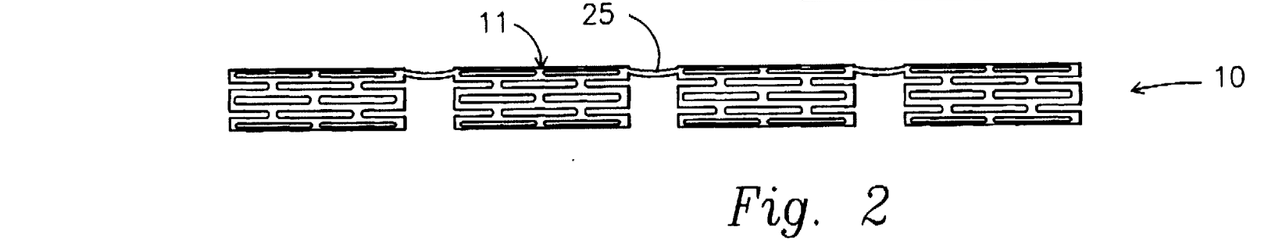
FIG. 2 shows a side view of the embodiment of FIG. 1 after the stents have been formed.
Figure 3:
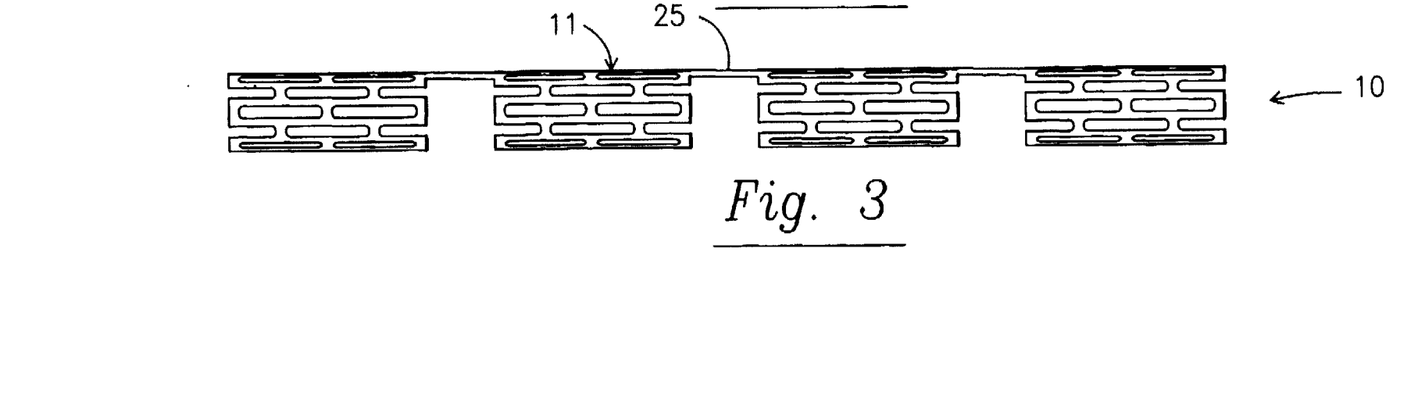
FIG. 3 shows an enlarged side view similar to that of FIG. 2.

With reference, first, to FIGS. 1–3, a first embodiment of the present invention is generally designated by the reference numeral 10. FIG. 1 shows the first embodiment 10 prior to forming of the stents from generally rectangular pieces 11 shown in the figure. In all of the embodiments of the present invention, each stent is formed from a rectangular piece such as the rectangular piece 11. As such, for ease of understanding, in each of the embodiments, these rectangular pieces will be referred to using the reference numeral 11.

As should be understood from FIG. 1, each rectangular piece 11 has a top edge 13 and a bottom edge 15 as well as side edges 17 and 19. Each rectangular piece 11 has a body 12 that includes a multiplicity of rows 14, 16 of slots 18, 8, respectively, with the slots 18 being separated by spaces 21 and with the slots 8 being separated by spaces 23. As should be understood from FIG. 1, the spaces 21, 23 are staggered with respect to one another in adjacent rows 14, 16. This configuration of slots and spaces is employed in each of the embodiments of the present invention. In the embodiment illustrated in FIGS. 1–3, adjacent pieces 11 forming stents are interconnected by virtue of flexible resilient bars 25. As seen in FIG. 1, in particular, the bars 25 are co-linear.

The rectangular piece 11 or tubular welded metal sheet used to form the stents is manufactured by using a laser cutting tool to prepare the slots 18 and 8 in either a sheet of metal or plastic. The laser tool cuts out each of the slots 18 and 8 from a preprogrammed pattern. Other methods of cutting can be employed such as photochemical etching, water jet cutting and similar mechanisms where energy in different forms are applied for cutting of the flat metal sheet or a tubular welded metal sheet. The metal can be stainless steel, titanium, nickel, a thermal alloy such as NITINOL or other metal compatible with a patient's vascular tissue. If metal is employed for the stent it can be coated with a biocompatible material such as polyurethane, polyethylene, polytetrafluroethylene, silicone, block co-polymers of polyurethane, polyethylene and silicone, a biodegradable polymer such as polylactic acid, poly glycollic acid, and or hydroxy butyrate or valerate co-polymer. Biocompatible material will not interfere with blood or blood vessel interior wall tissue. The polymers can include anticoagulant agents, growth factor and like agents for reducing the reaction of blood to foreign surfaces.

Plastics employed to make the stent can be polyethylene, polyurethane, silicone or co-polymer of polyurethane and polyethylene compatible with the vascular tissue of a patent.

In a further aspect, when the device as seen in FIG. 1 is assembled into the multiple stent 10 as seen in FIGS. 2 and 3, the body 12 is formed into a roll and the edges 13 and 15 are fused together by any suitable means such as plasma energy fusing, LASER fusing, ultrasonic fusing, spot welding or seam welding. This feature is in common with all of the embodiments of the present invention. The body can be formed in a roll and fused together before forming the slots over a solid tubular structure.

Figures 4, 5:
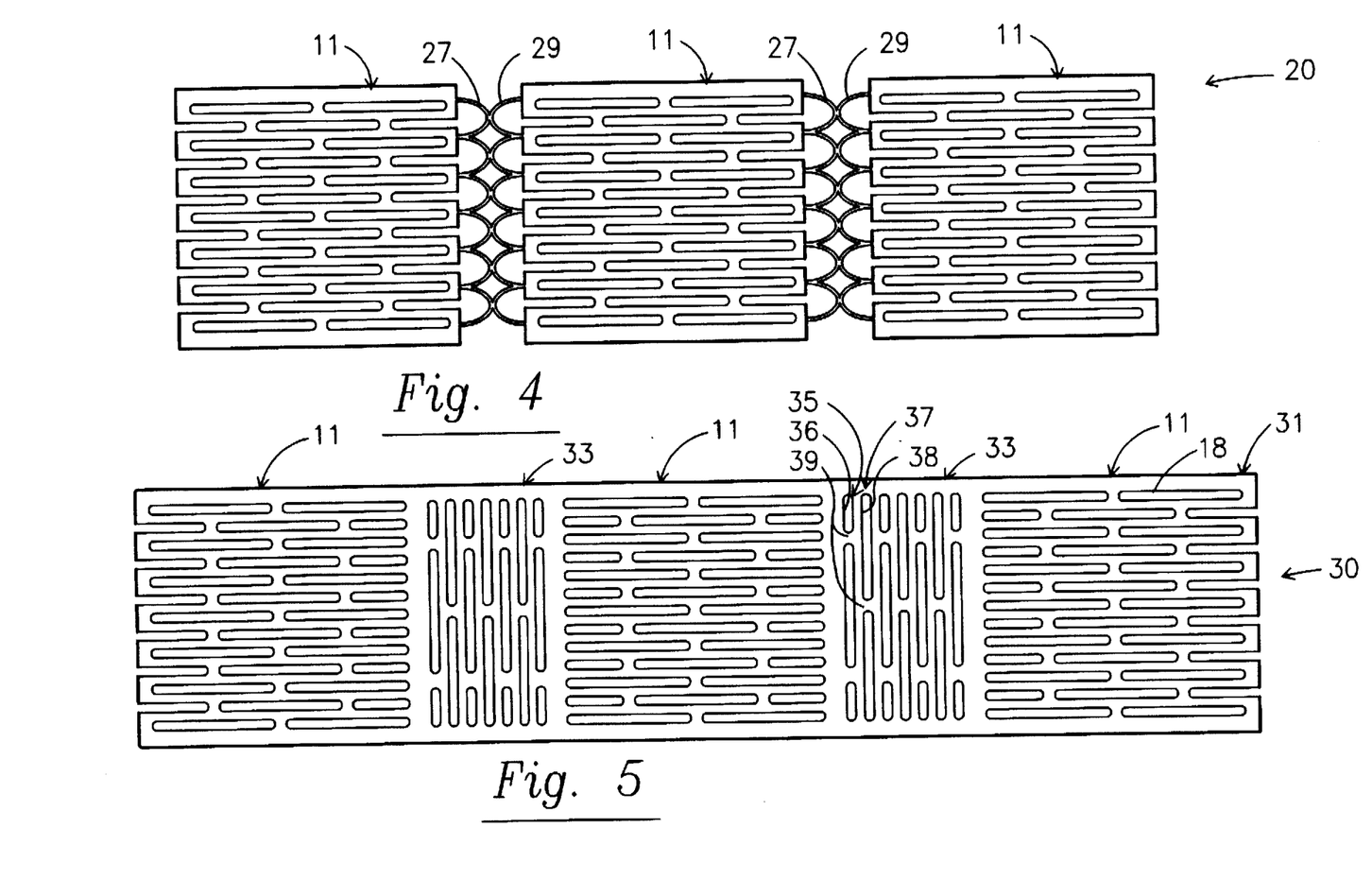
FIG. 4 shows a side view of a second embodiment of the present invention.
FIG. 5 shows a side view of a third embodiment of the present invention.

With reference to FIG. 4, a second embodiment of multiple interconnected stents is designated by the reference numeral 20 and includes a plurality of pieces 11 forming stents as explained above. Adjacent stents are interconnected by virtue of U-shaped members 27, 29 that are fused together at various points and interconnected to each stent as shown in FIG. 4. These interconnectors 27, 29 are flexible and resilient.

FIG. 5 shows a third embodiment of the present invention generally designated by the reference numeral 30 and including a plurality of rectangular pieces 11 formed in a single sheet 31 integrally incorporating interconnectors 33, each of which consists of a plurality of rows 35, 37 of slots 36, 38 with each row of slots 36, 38 having spaces 39 between adjacent slots that are staggered in adjacent rows. The slots 36, 38 are orthogonal to the slots 8 and 18 of the rectangular piece 11.

Figure 6:
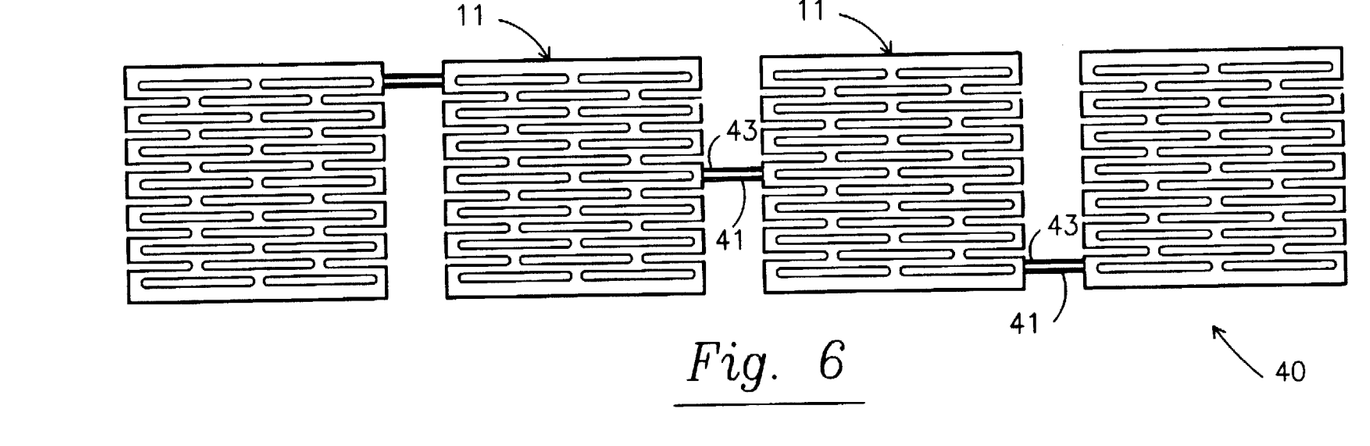
FIG. 6 shows a side view of a fourth embodiment of the present invention.

FIG. 6 shows a fourth embodiment of the present invention generally designated by the reference numeral 40 and including a plurality of pieces 11 interconnected by double bars 41, 43. These double bars 41, 43 are similar to the single bars 25 in the first embodiment illustrated in FIGS. 1–3.

However, as seen in FIG. 6, different sets of double bars 41, 43 are vertically staggered with respect to one another.

Figure 7:
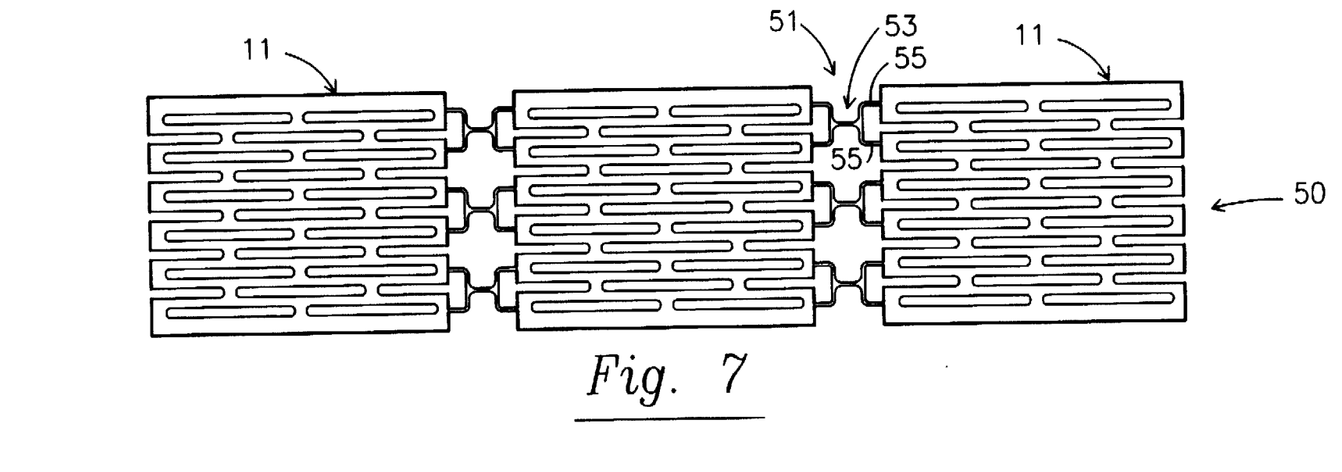
FIG. 7 shows a side view of a fifth embodiment of the present invention.

FIG. 7 shows a fifth embodiment of the present invention generally designated by the reference numeral 50 and including a plurality of pieces 11 interconnected by interconnectors 51 consisting of a plurality of vertically spaced connectors 53, each resembling the letter "H" with additional horizontal legs 55 connecting the "H"-shaped connector 53 to each piece 11.

Figure 8:
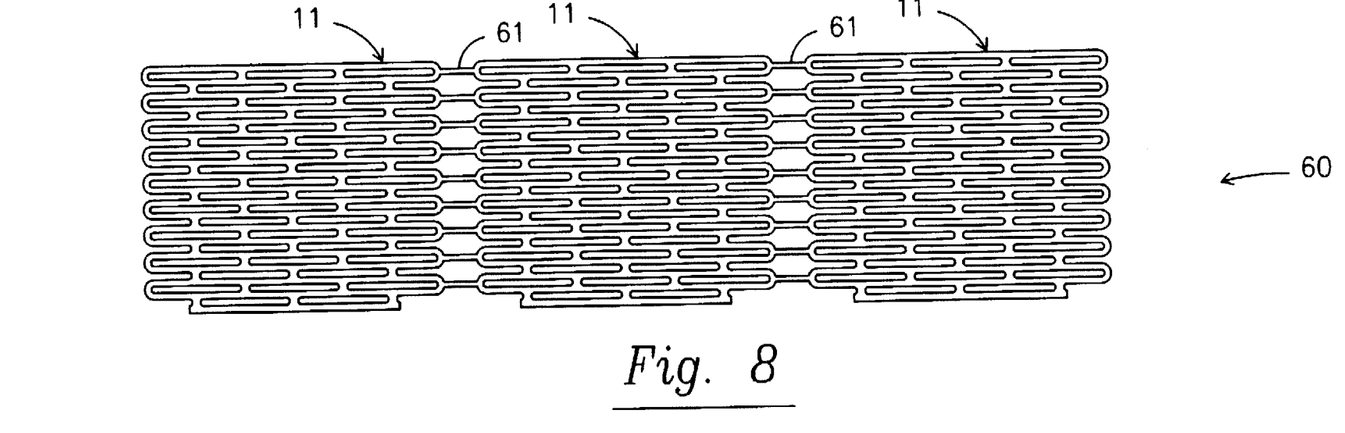
FIG. 8 shows a side view of a sixth embodiment of the present invention.

FIG. 8 shows a sixth embodiment of the present invention generally designated by the reference numeral 60 and including a plurality of pieces 11 with adjacent pieces 11 being interconnected by a multiplicity of vertically spaced bars 61. This embodiment is similar to the embodiment of FIGS. 1–3 except that a multiplicity of bars 61 are employed instead of the single bars 25 of the FIGS. 1–3 embodiment.

Figure 9:
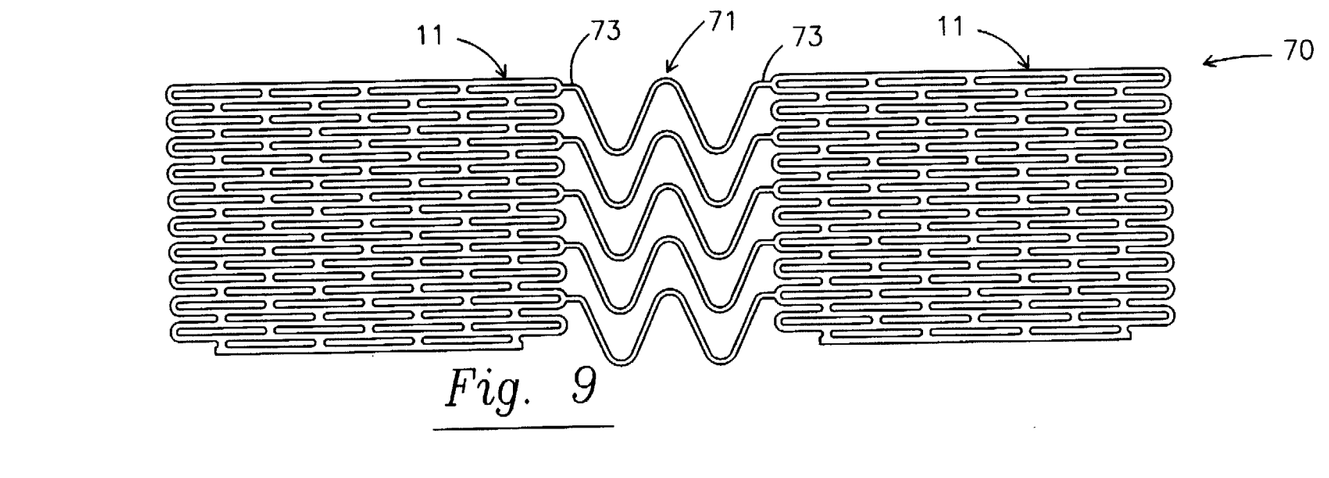
FIG. 9 shows a side view of a seventh embodiment of the present invention.

FIG. 9 shows a seventh embodiment of the present invention generally designated by the reference numeral 70 and including a plurality of pieces 11 interconnected together by a plurality of vertically spaced interconnectors 71, each one of which is flexible and resilient and resembles the letter "W". At the lateral sides of each connector 71, a short lateral section 73 is provided to connect the connector 71 to each adjacent piece 11.

Figure 19:
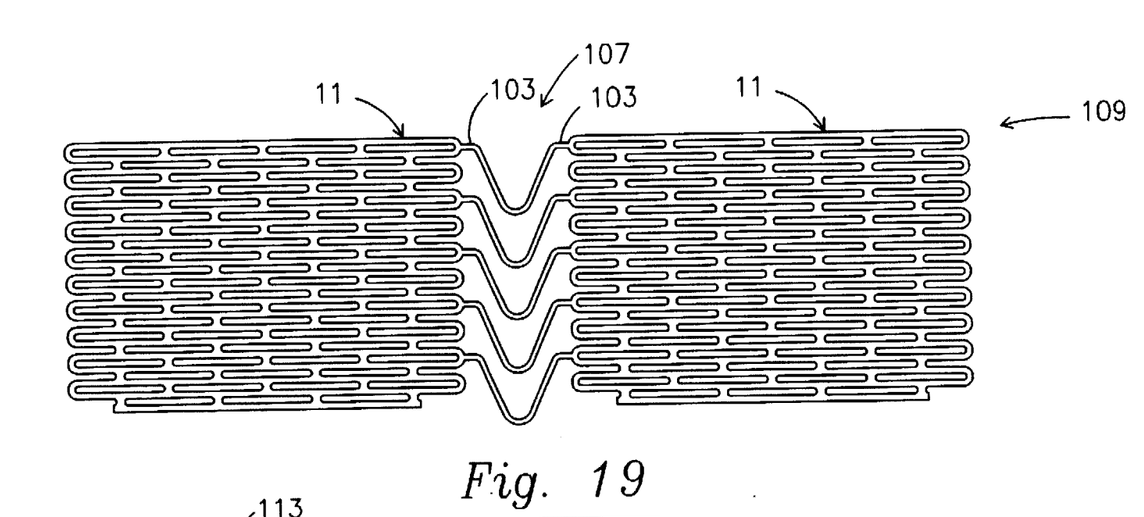
FIG. 19 shows a side view of an eighth embodiment of the present invention.

FIG. 19 shows an eighth embodiment of the present invention generally designated by the reference numeral 109 and including a plurality of pieces 11 interconnected together by a plurality of vertically spaced interconnections 107 each one of which is flexible and resilient and resembles the letter "V". At lateral sides of each connector 107 is a short lateral section 103 provided to connect the connector 109 to each adjacent piece 11.

Figures 26, 27, 28, 29:
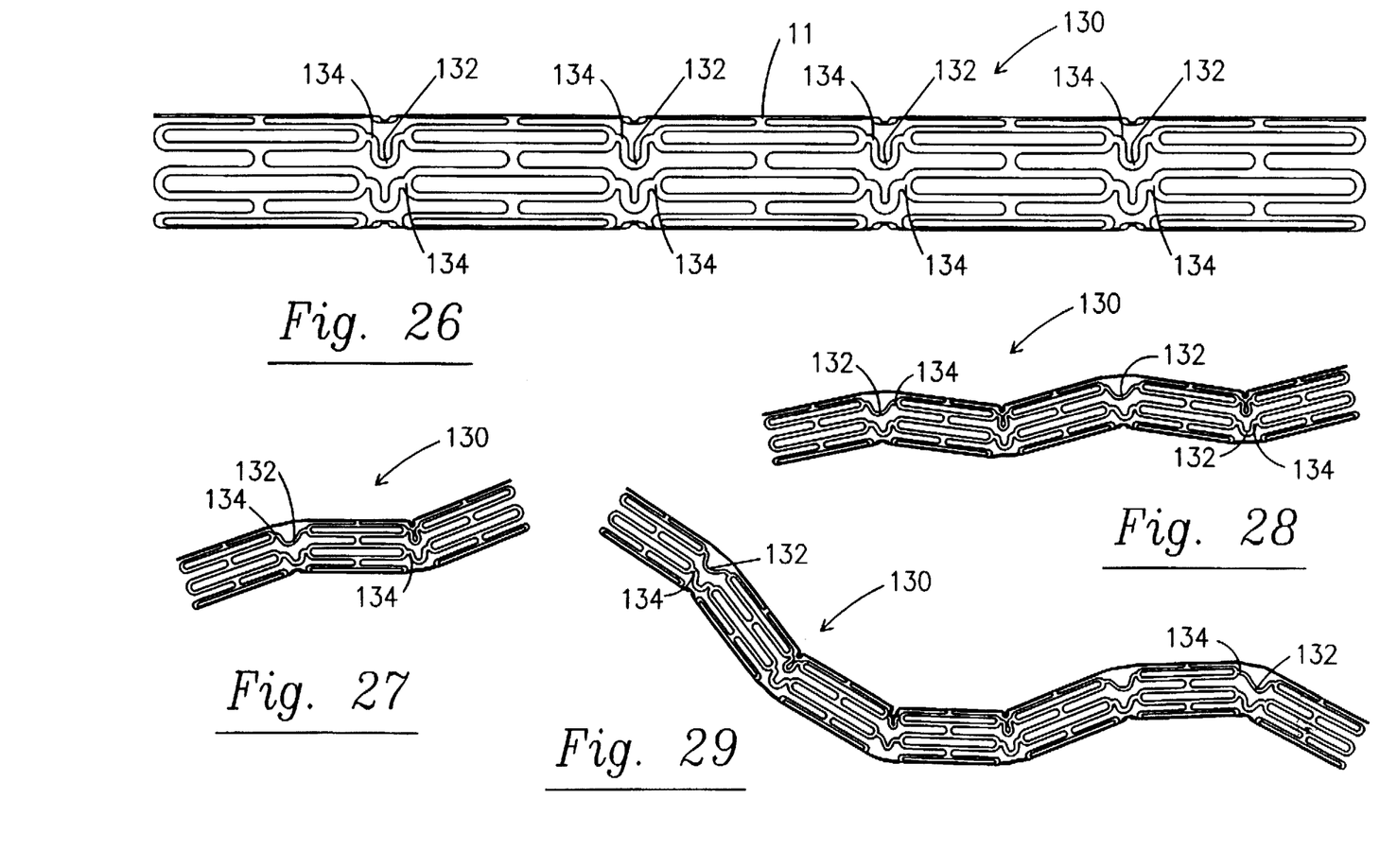
FIG. 26 shows a side view of a ninth embodiment of the present invention.
FIG. 27 shows a top plan view of the multiple stent of FIG. 26 with three stent pieces in an articulated position.
FIG. 28 shows a top plan view of the multiple stent of FIG. 26 with five stent pieces in an articulated position.
FIG. 29 shows a top plan view of the multiple stent of FIG. 26 with seven stent pieces in an articulated position.

FIG. 26 shows a ninth embodiment of the invention generally designated by the reference numeral 130 and including a plurality of pieces interconnected together by a plurality of vertically spaced interconnections 132 each one of which is flexible and resilient and resembles the letter "U". At lateral sides of each connector 132 is a short lateral section 134 provided to connect the connector 132 to each adjacent piece 11. The plurality of vertically spaced interconnections 132 are used to traverse a blood vessel. These interconnections 132 become rigid after expansion of the stent in place.

Figure 10:
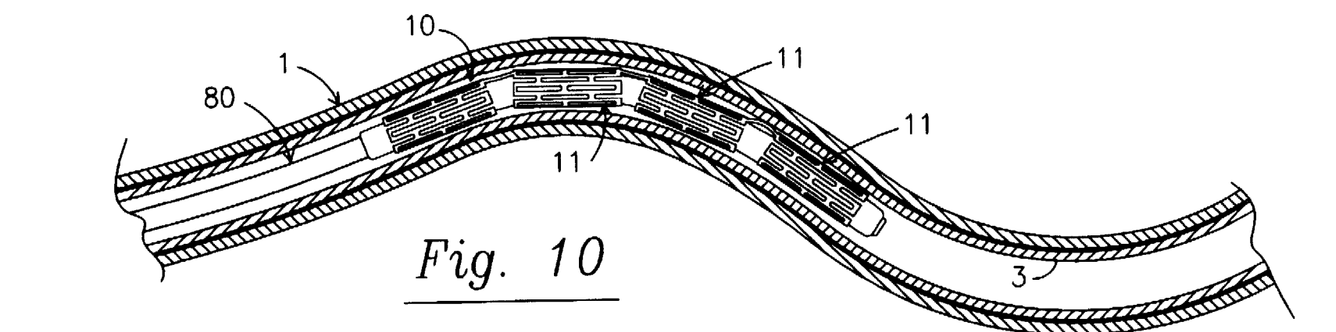
FIG. 10 shows a side view, partially in cross-section, of a multiple stent in accordance with the teachings of the present invention as it is being inserted within a blood vessel.
Figure 11:
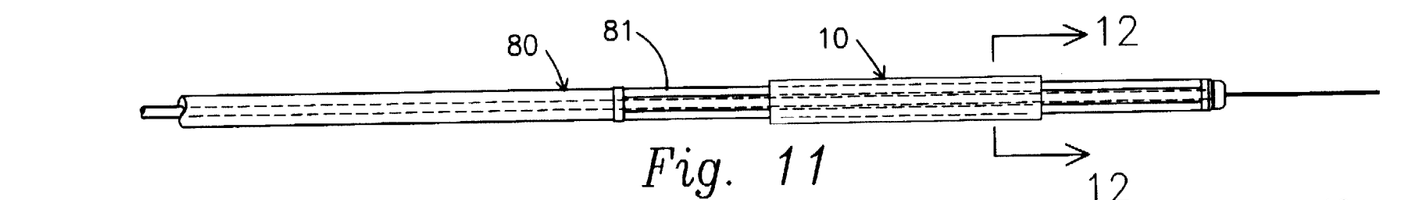
FIG. 11 shows a further side view of a stent attached over an insertion mechanism.
Figure 12:
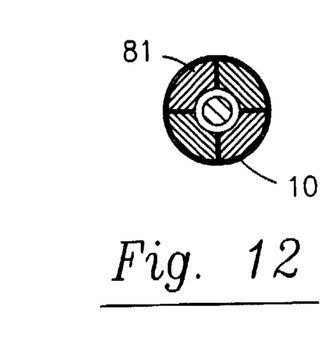
FIG. 12 shows a cross-sectional view along the line 12—12 of FIG. 11.
Figure 13:
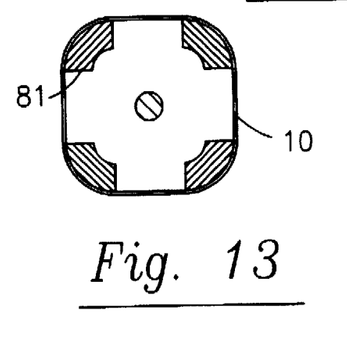
FIG. 13 shows a view similar to that of FIG. 12 but with the stent expanded.

FIG. 10 shows a side view, partially in cross-section, of the multiple stent 10 of the embodiment of FIGS. 1–3 as contained within a blood vessel 1. An appliance 80 is shown inserted through the pieces 11 to convey the entire multiple stent 10 to a desired location within the blood vessel 1. FIG. 11 shows the device 80 which is better seen with reference to FIGS. 12, 13, 16, 17 and 18. As seen, the device 80 includes a plurality of expander blocks 81 mounted on a spreader mechanism 83 including legs 85, 87 pivoted together at a pivot 89 and interconnected to an actuator mechanism 91 at the pivots 93. A wire 95 extends through the tube 97 and connects to the actuator 91 whereby when the wire 95 is pulled in the direction of the arrow 99, the actuator 91 moves to the right in the view of FIG. 18 to cause separation of the blocks 81 to the position shown in FIGS. 13 and 18 whereby the stent 10 is expanded to engage the walls 3 of the blood vessel 1.

Figure 14:
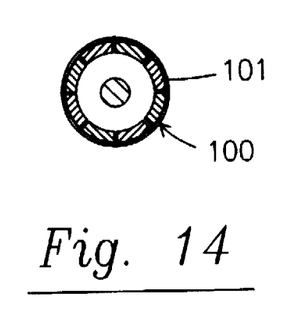
FIG. 14 shows a view similar to FIG. 12 of a different stent configuration.
Figure 15:
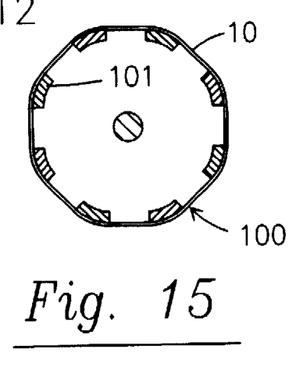
FIG. 15 shows a view similar to that of FIG. 13 with the stent of FIG. 14 expanded.
Figure 16:
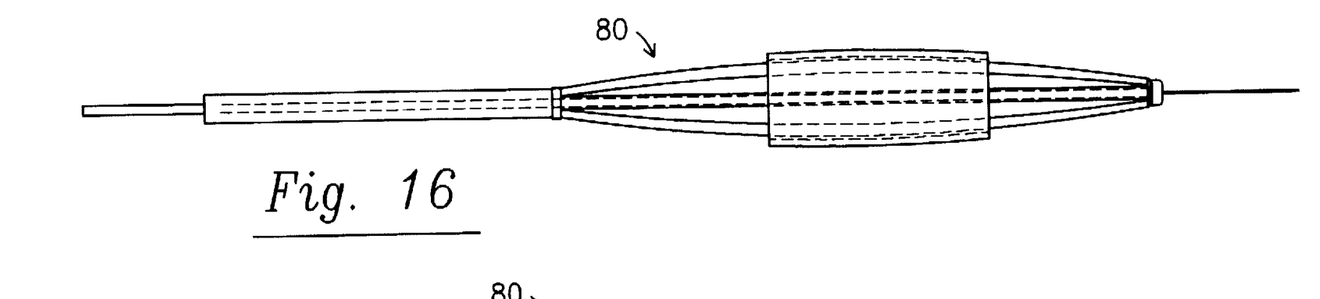
FIGS. 16 and 17 show an expanding mechanism in the expanded and closed configurations, respectively.
Figure 17:
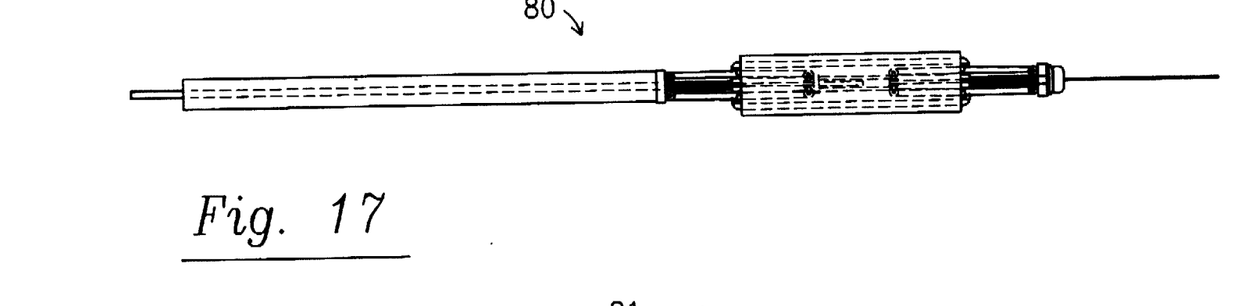
Figure 18:
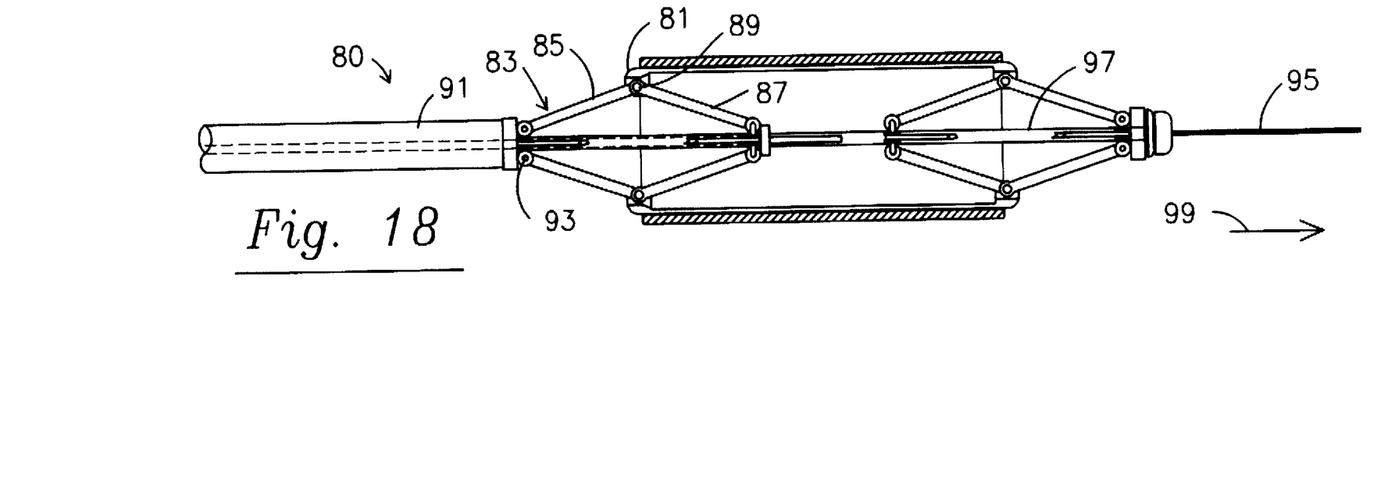
FIG. 18 shows further details of the mechanical expanding mechanism shown in FIGS. 16 and 17.

Other views of the device 80 are also seen in FIGS. 16 and 17 with FIGS. 14 and 15 showing an alternative insertion device 100 having eight blocks 101 rather than the four blocks 81 of the device 80. The insertion device 100 spreads the forces of enlargement of the stents 10 more uniformly around the circumference thereof.

The stents employed in this invention are about 1.5–2.5 mm in length and the interconnections about 0.30 mm to 0.60 mm in length. The total length of an interconnected stent is 5 mm to 60 mm in length to form segments of the rigid slotted stents and flexible interconnections.

If desired, the various embodiments of multiple stents disclosed hereinabove may be suitably coated with a polymeric or biologic material to enhance retention within the body. Details of such coating and method of coating are set forth in Applicant's co-pending U.S. patent application Ser. No. 08/689,290.

Figure 20:
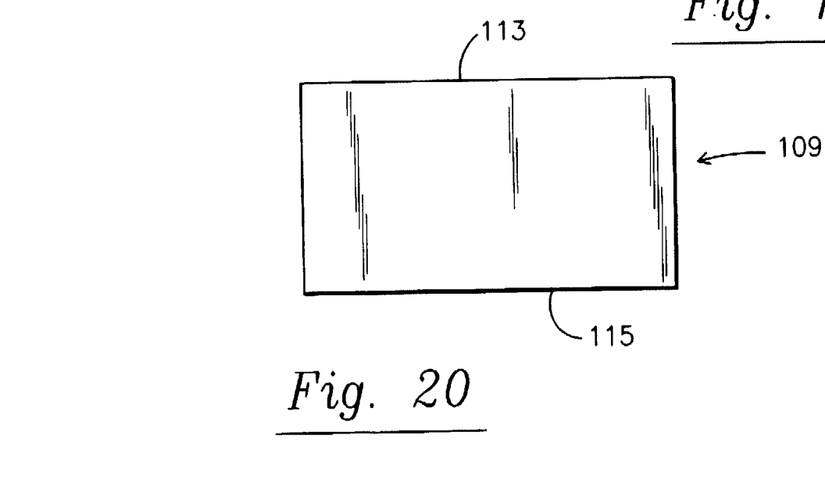
FIG. 20 shows a rectangular structure prior to undergoing the process of preparing a stent as shown in FIG. 3.
Figure 21:
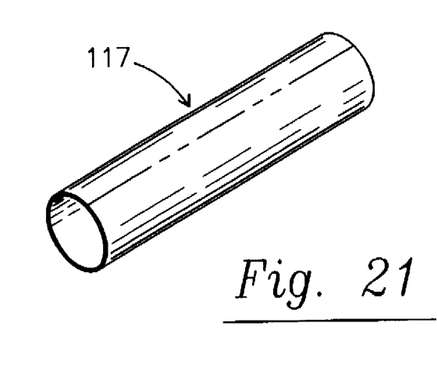
FIG. 21 shows a seamless tube prepared from the structure of FIG. 20.
Figures 23, 25:
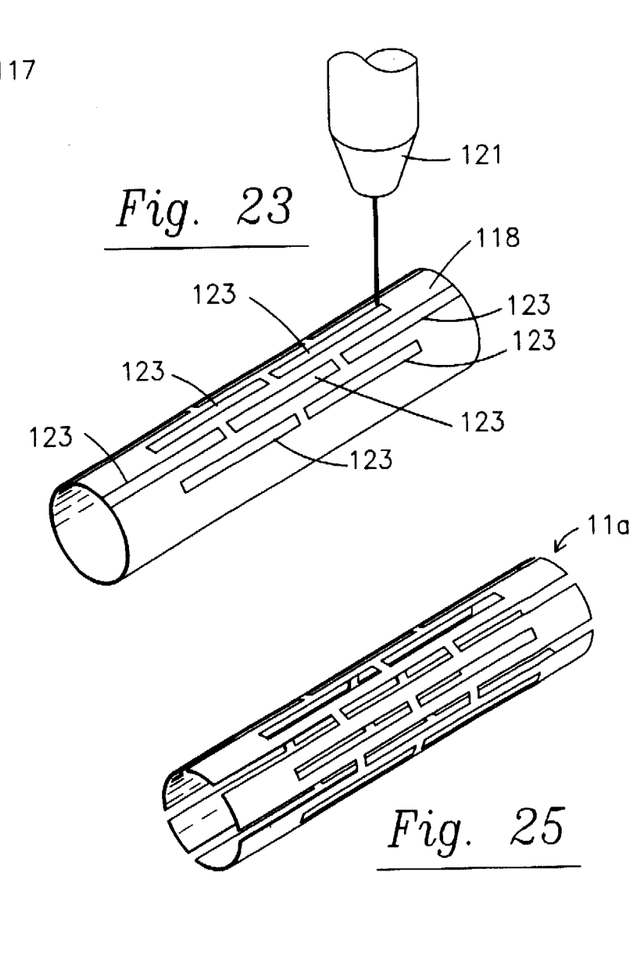
FIG. 23 shows the selective removal of the polymer film to provide a pattern in the tube.
FIG. 25 shows one portion of the stent produced by the process shown in FIGS. 19–24.

An alternative process for preparing a stent 11a as shown in FIG. 25 starts with a stainless steel, titanium or alloy thereof rectangular sheet 111 (FIG. 20) which has edges 113 and 115 fused by an ultrasonic beam to produce the tube 117 shown in FIG. 21. Alternatively, the tube can be formed by spot welding and seam welding.

Figures 22, 24:
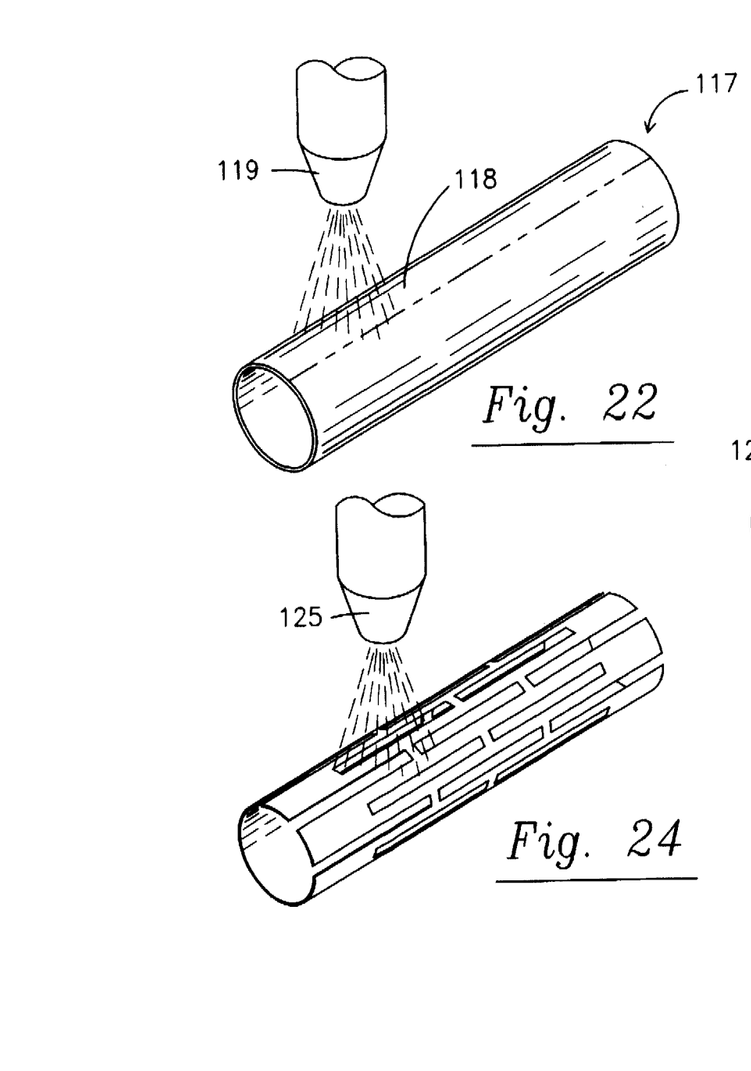
FIG. 22 shows deposition of a thin polymer film on the seamless tube of FIG. 21.
FIG. 24 shows the chemical etching away of unprotected metal.

Thereafter a polymer film 118 of about 10–20 microns is deposited on tube 117 by a spray nozzle 119 as seen in FIG. 22. The polymer film can be sprayed on the outside or inside or both sides of the tube 117. The preferred polymer is polytetraflouroethylene. A portion of the polymer film 118 is selectively removed with a tool 121 as show in FIG. 23 to reveal the metal below 123. Alternatively, a UV laser can be programmed to remove the polymer layer. An infrared laser with suitable wavelength can be used. The metal 123 is chemically etched 125 away or removed by selective electrolysis as shown in FIG. 24 to present the stent 11a pattern shown in FIG. 25. Alternatively, a Nd-Yag laser specific to the metal 123 can be used to remove the desired portion of metal. The rectangular sheet 111 is approximately 25–50 mils thick and therefore the etching, laser beam or electrolysis removes metal of such thickness.

The multiple interconnected stents of this invention are coated with a thin layer of anti-thrombogenic coatings to prevent the adherence of blood clots to the surface.

The polymer material applied to the stents can be applied by plasma vapor deposition where the stent tube is kept in a chamber and the polymer material is deposited under controlled conditions of temperature and pressure.

As such, an invention has been disclosed in terms of preferred embodiments thereof which fulfill each and every one of the objects of the invention as set forth hereinabove and provide new and useful embodiments of multiple interconnected stents of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

I claim:

1. A multiple linear segment stent comprising:
   a) at least first and second linear segments, each linear segment formed from a generally rectangular body formed into a tube, said body having top and bottom edges fused together to form said tube, said body having a plurality of parallel rows of slots, each row having a plurality of longitudinal slots separated from one another by spaces, said spaces being laterally staggered in adjacent rows;
   b) said linear segments being interconnected together by flexible interconnection elements attached at juxtaposed positions on adjacent linear segments for use in traversing a blood vessel, said interconnection elements becoming rigid and increasing in length upon expansion of the stent in the blood vessel.

2. The multiple linear segment stent of claim 1, wherein each said interconnection element comprises at least one U-shaped member on said first linear segment attached to said second liner segment.

3. The multiple linear segment stent of claim 4, wherein the first and second linear segments are connected by a plurality of U-shaped members.

4. The multiple stent of claim 1, wherein said stents are formed in a single rectangular body.

5. The multiple stent of claim 4, wherein said interconnection means comprises a plurality of interconnection slots in said single rectangular body orthogonal to said slots of said stents.

6. The multiple stent of claim 1, wherein said interconnection means is "H" shaped.

7. The multiple stent of claim 6, including a plurality of "H" shaped interconnection means.

8. The multiple stent of claim 1, wherein said interconnection means is "W" shaped.

9. The multiple stent of claim 1, wherein said stents are coated with a polymeric coating.

10. The multiple stent of claim 1, wherein said stents are coated with a biological coating.

11. The multiple stent of claim 1, wherein said interconnection means is "V" shaped.

12. The multiple stent according to claim 1 wherein there are at least three stents interconnected by flexible interconnection means.

* * * * *